(12) United States Patent
Kadziauskas et al.

(10) Patent No.: US 7,037,296 B2
(45) Date of Patent: May 2, 2006

(54) CURVED MULTI-PURPOSE PHACOEMULSIFICATION NEEDLE

(75) Inventors: Kenneth E. Kadziauskas, Coto De Caza, CA (US); Mark E. Steen, Chino Hills, CA (US); Thomas B. Sutton, Irvine, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 10/817,684

(22) Filed: Apr. 2, 2004

(65) Prior Publication Data
US 2004/0193121 A1    Sep. 30, 2004

Related U.S. Application Data

(63) Continuation-in-part of application No. 10/115,626, filed on Apr. 4, 2002, now Pat. No. 6,958,056.

(51) Int. Cl.
*A61M 35/00* (2006.01)

(52) U.S. Cl. .................................. 604/294; 604/272

(58) Field of Classification Search .............. 604/22, 604/264, 272, 289, 290, 294; 606/107, 167, 606/170
See application file for complete search history.

(56) References Cited

U.S. PATENT DOCUMENTS

| | | | |
|---|---|---|---|
| 3,732,858 A | 5/1973 | Banko | |
| 3,844,272 A | 10/1974 | Banko | |
| 4,047,532 A * | 9/1977 | Phillips et al. | |
| 4,531,943 A * | 7/1985 | Van Tassel et al. | |
| 4,689,040 A * | 8/1987 | Thompson | |
| 4,816,018 A | 3/1989 | Parisi | |
| 4,959,049 A | 9/1990 | Smirmaul | |
| 5,100,390 A | 3/1992 | Lubeck et al. | |
| 5,112,339 A | 5/1992 | Zelman | |
| 5,213,569 A * | 5/1993 | Davis | |
| 5,242,385 A | 9/1993 | Strukel | |
| 5,254,106 A | 10/1993 | Feaster | |
| 5,290,267 A | 3/1994 | Zimmermann | |
| 5,295,980 A * | 3/1994 | Ersek | |
| 5,451,229 A | 9/1995 | Geuder et al. | |
| 5,464,389 A | 11/1995 | Stahl | |
| 5,484,398 A | 1/1996 | Stoddard | |
| 5,515,871 A | 5/1996 | Bittner et al. | |
| 5,690,641 A * | 11/1997 | Sorensen et al. | |
| 5,725,495 A * | 3/1998 | Strukel et al. | |
| 5,733,266 A | 3/1998 | Gravlee, Jr. | |
| 5,743,871 A | 4/1998 | Strukel et al. | |
| 5,746,713 A | 5/1998 | Hood et al. | |
| 5,755,700 A * | 5/1998 | Kritzinger et al. | |

(Continued)

FOREIGN PATENT DOCUMENTS

EP    1 129 681 A1    9/2001

(Continued)

*Primary Examiner*—LoAn H. Thanh
(74) *Attorney, Agent, or Firm*—Advanced Medical Optics, Inc.

(57) ABSTRACT

A multipurpose phacoemulsification needle includes a needle body having a lumen therethrough for aspiration of fluids and tissue. A needle body includes a proximal end adapted for attachment to a phacoemulsification handpiece, a curved portion and a tip portion disposed at a distal end of the needle body. The tip portion includes a truncated hemisphere having a flat surface thereon and a port disposed in the flat surface. The truncated hemisphere includes a rounded surface of sufficient area to enable capsule polishing and when driven in an ultrasonic mode, the needle is also suitable for irrigation and aspiration as well as phacoemulsification of lens tissue.

6 Claims, 2 Drawing Sheets

U.S. PATENT DOCUMENTS

| | | | |
|---|---|---|---|
| 5,788,679 A * | 8/1998 | Gravlee, Jr. | 604/272 |
| 5,836,926 A * | 11/1998 | Peterson et al. | |
| 5,871,470 A | 2/1999 | McWha | |
| 5,980,529 A | 11/1999 | Strukel | |
| 5,993,409 A * | 11/1999 | Maaskamp | |
| 6,159,175 A | 12/2000 | Strukel et al. | |
| 6,398,754 B1 | 6/2002 | Sutton et al. | |
| 6,402,734 B1 * | 6/2002 | Weiss | 604/521 |
| 6,491,670 B1 * | 12/2002 | Toth et al. | |
| 6,554,809 B1 | 4/2003 | Aves | |
| 2004/0199192 A1 * | 10/2004 | Akahoshi | |
| 2004/0267211 A1 * | 12/2004 | Akahoshi | |

FOREIGN PATENT DOCUMENTS

| | | |
|---|---|---|
| EP | 1 212 995 A2 | 6/2002 |

* cited by examiner

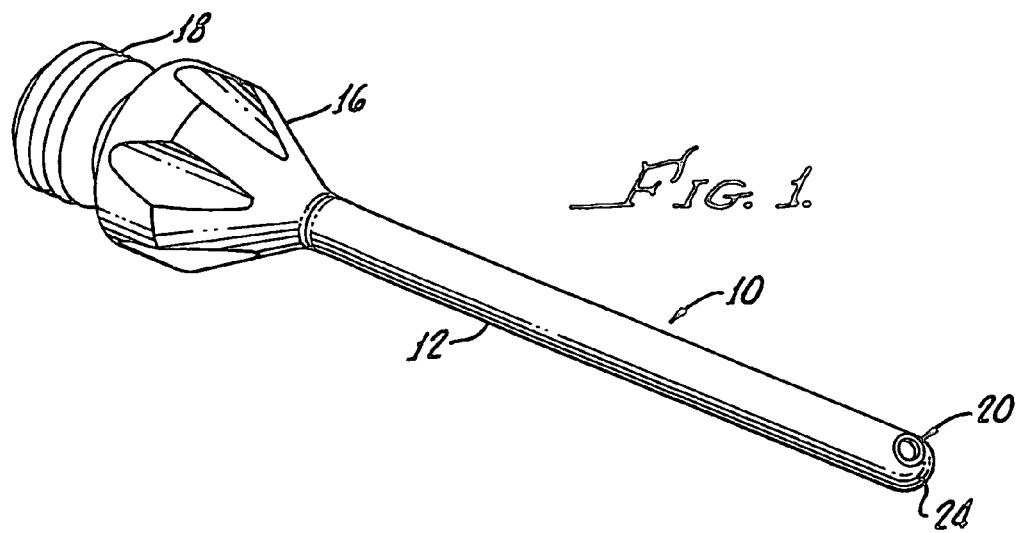
FIG. 1.
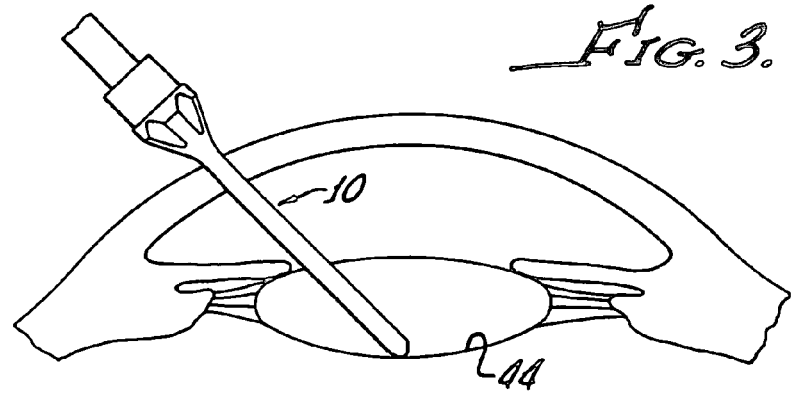
FIG. 2.
FIG. 3.

CURVED MULTI-PURPOSE PHACOEMULSIFICATION NEEDLE

This application is a continuation-in-part of U.S. Ser. No. 10/115,626 filed Apr. 4, 2002 now U.S. Pat. No. 6,958,056.

The present invention generally relates to phacoemulsification needles and is more particularly directed to a multipurpose phacoemulsification needle.

Phacoemulsification refers to a method of lens and cataract extraction from an eye. The procedure includes an ultrasonically vibrated needle which is inserted through a very small incision of the cornea in order to provide energy for fragmenting the lens and cataract which then can be aspirated and removed through the incision.

The needle is supported by a handpiece interconnected with a console which provides electrical power to the handpiece as well as a supply of irrigation fluid and a vacuum source for aspiration of fragmented tissue and liquids.

The handpiece typically includes piezoelectric crystals or magnetostrictive elements which are coupled to the needle.

Often several needle types are utilized in the phacoemulsification procedure. For example, many needles utilize a relatively sharp surface in order to both enhance phacoemulsification and to break up the lens nucleus and cortex. However, any sharp edges can inadvertently cut the capsule surrounding the lens which may impair effective healing and prevent satisfactory visual recovery.

It is necessary, however, to remove soft cortical remnants of cataract tissue against the capsule and this often necessitates a second needle, or tool. This process effectively vacuums the internal surface of the lens capsule and is known as polishing.

The present invention provides for a multipurpose phacoemulsification needle suitable for both phacoemulsification of cataract and lens tissue as well as being affective for polishing the capsule.

SUMMARY OF THE INVENTION

A multipurpose phacoemulsification needle in accordance with the present invention generally includes a needle body having a lumen therethrough for aspiration of fluid and tissue. The needle body includes a proximal end adapted for attachment to a phacoemulsification handpiece and a distal end having a tip portion.

More specifically, the tip portion includes a truncated hemisphere having a flat surface thereon and a port disposed in the flat surface with the port communicating with the needle body lumen.

The tip can also be described as having a convex surface of revolution about a centerline of the tip portion which is defined by an arc extending from a circumference of the needle body to the tip portion centerline.

The surface of revolution provides for a rounded portion which includes sufficient area for polishing the eye lens capsule.

More particularly, the flat surface may extend from a centerline of the top portion to a tip portion circumference and include a bevel in the flat surface surrounding the port. This features insures that there will be no or minimal sharp edges in the needle distal end.

Still more particularly, the needle flat surface may be disposed at about a 45° angle with respect to the tip potion centerline.

The needle body may include a curved portion disposed adjacent the distal end tip portion which includes a curvature in a plane not including the flat surface.

Preferably, the plane is perpendicular to the flat surface and in one embodiment, the flat surface faces inward from an arc established by the needle body curved portion and in another embodiment, the flat surface faces outwardly from an arc established by the needle body curved portion.

The curved needle embodiments have additional advantage in the generation of cavitational energy, manipulating tissue within the eye during surgery and accessing cortex material from difficult to access locations within the eye during irrigation and aspiration.

BRIEF DESCRIPTION OF THE DRAWINGS

The advantage of the present invention may be more readily understood by consideration of the following detailed description, particularly in conjunction with the accompanying drawings in which:

FIG. 1 is perspective view of a multipurpose phacoemulsification needle in accordance with the present invention generally showing a needle body having a proximal and distal end with a tip portion disposed at the distal end;

FIG. 2 is a cross-sectional view of the tip portion of the needle shown in FIG. 1;

FIG. 3 is a representation of the needle function in polishing an eye capsule;

DETAILED DESCRIPTION

Figure 4:
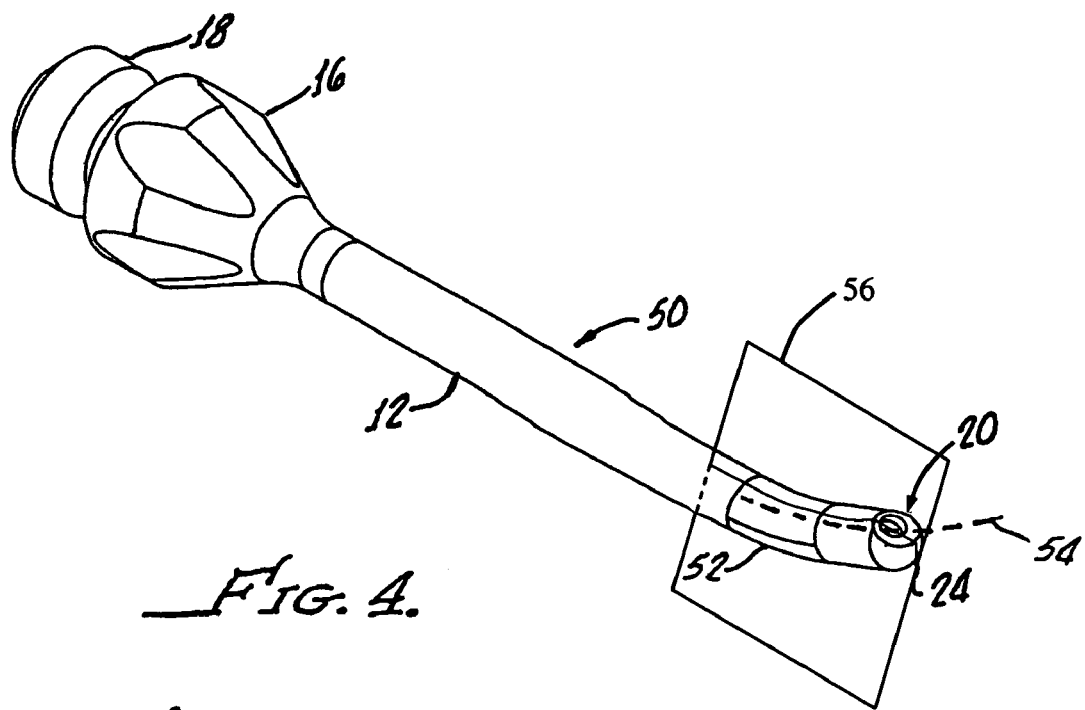
FIG. 4 is a perspective view of an alternative embodiment of the present invention similar to the embodiment shown in FIG. 1 but with a curved needle body portion.

With reference to FIG. 1, there is shown a multipurpose phacoemulsification needle 10 generally having a needle body 12 having a lumen 14 therethrough as shown in FIG. 2. The needle body includes a proximal end 16 which may include a threaded portion 18 which adapts the needle for attachment to a phacoemulsification handpiece, not shown. The needle 10 may be formed from a single piece of material suitable for phacoemulsification needle as is well known in the art.

A tip portion 20 of the needle body 12 includes a truncated hemisphere 24 having a flat surface 26 thereon.

The hemispherical surface 24 is formed by a convex surface of revaluation about a centerline 30 of the tip portion 20 defined by an arc extending from a circumference 32 of the needle 12 to the centerline 30.

The hemispherical or rounded surface 24 is of sufficient area for polishing an eye lens capsule as will be hereinafter described.

A port 38 is disposed in a flat surface 26 with the port 38 communicating with the needle body lumen 14 as most clearly shown in FIG. 2. A bevel 40 in the flat surface 26 surrounding the port, provides for a smooth entry through the port 38 and eliminates any sharp edges.

Preferably, the flat surface 26 is at an angle at about 45° with a centerline 30 and the port diameter, D, is between 0.1 mm to about 0.5 mm.

Because of the rounded surface 24, and position of the port at a 45° angle, the needle 10 is well suited for either cataract extraction and/or Irrigation and Aspiration (I/A) of the cortex.

As illustrated in FIG. 3, the curved nature of the tip portion 20 and the significant area of the rounded portion 24, enables the surgeon to work close to a capsule and, in fact polish the capsule 44. Through the use of ultrasonic energy the needle may also be used (during I/A irrigation aspiration function) to remove cortex. Thus, a specific and important advantage of the present invention is that it eliminates the current need to use a separate handpiece to perform the I/A of a phacoemulsification procedure.

The present invention is easily distinguished over heretofore available phacoemulsification, such as for example, set forth in U.S. Pat. No. 5,980,529 which illustrates an off axis entry port but utilizes a angular or pointed end which is not amendable for lens capsule 44 polishing, and accordingly, is not a multipurpose needle.

With reference to FIG. 4, there is shown an alternative embodiment 50 in accordance with the present invention with common reference characters indicating substantially similar or identical elements of the invention as hereinabove described in connection with the embodiment shown in FIG. 1.

The multipurpose phacoemulsification needle 50 includes a curved portion 52 adjacent to the tip portion 20 having a curvature 54 in a plane 56 not including the flat surface 26, see FIG. 2. Preferably, the flat surface 26 is perpendicular to the plane 56 established by the curved portion curvature, or arc, 54.

In the embodiment 50, a flat surface 26 faces inwardly from the arc 54 established by the needle body curved portion 52.

Figure 5:
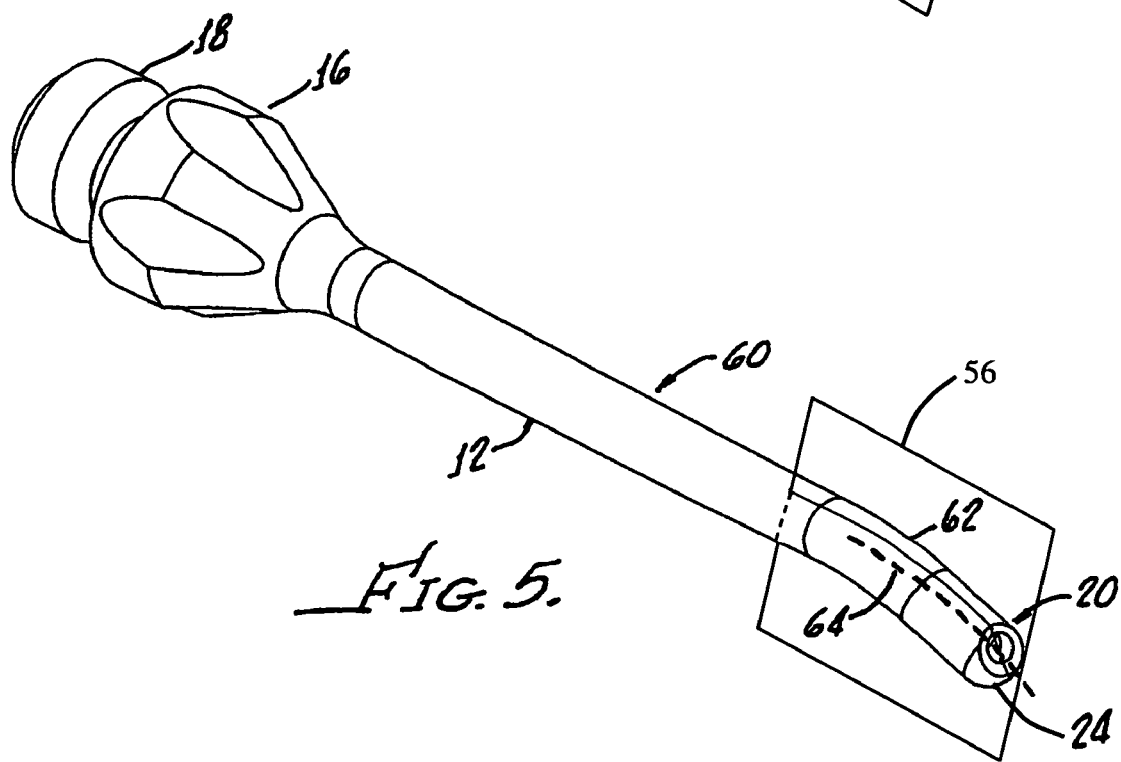
FIG. 5 is a perspective view of yet another embodiment of the present invention similar to the embodiment shown in FIG. 4 with a curved needle body portion, the curve being opposite that shown in FIG. 4.

With reference to FIG. 5, there is shown yet another embodiment 60 of a multipurpose phacoemulsification needle in accordance with the present invention with common reference numbers representing identical or substantially similar elements as hereinabove discussed in connection with FIGS. 1 and 4.

The phacoemulsification needle 60 is similar to the embodiment 50 shown in FIG. 4 except that a curved portion 62 is provided proximate the tip 20 which establishes an arc 64 opposite the arc 54 shown in FIG. 4 and in which the flat surface 64 faces outwardly from the arc 64 established by the needle body curved portion 62.

As hereinabove noted, these various phacoemulsification needle embodiments have the additional advantage in the generation of cavitational energy, manipulating tissue within the eye during surgery, as hereinabove noted, and accessing cortex material from difficult to access locations within the eye during irrigation and aspiration. The angle of curvature, or arc, 54, 64 may vary in the angle of the curvature or arc, the curvature depending upon the specific use intended for the needle 50, 60.

Although there has been hereinabove described a specific curved multi-purpose phacoemulsification needle in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A multi-purpose phacoemulsification needle comprising:
    a needle body having a lumen therethrough for aspiration of fluid and tissue;
    a needle body proximal end adapted for attachment to a phacoemulsification handpiece;
    a needle body distal end having a tip portion, said tip portion comprising:
        a truncated hemisphere having a flat surface thereon; and
        a port disposed in said flat surface, said port communicating with the needle body lumen; and
    a needle body curved portion disposed adjacent the tip portion and having a curvature in a plane not including said flat surface;
    said plane is perpendicular to said flat surface;
    said flat surface faces inwardly from an arc established by the needle body curved portion.

2. A multi-purpose phacoemulsification needle comprising:
    a needle body having a lumen therethrough for aspiration of fluid and tissue;
    a needle body proximal end adapted for attachment to a phacoemulsification handpiece;
    a needle body distal end having a tip portion, said tip portion comprising:
        a truncated hemisphere having a flat surface thereon; and
        a port disposed in said flat surface, said port communicating with the needle body lumen; and
    a needle body curved portion disposed adjacent the tip portion and having a curvature in a plane not including said flat surface;
    said plane is perpendicular to said flat surface;
    said flat surface faces outwardly from an arc established by the needle body curved portion.

3. A multi-purpose phacoemulsification needle comprising:
    a needle body having a lumen therethrough for aspiration of fluid and tissue;
    a needle body proximate end adapted for attachment to a phacoemulsification handpiece;
    a needle body distal end having a tip portion, said tip portion comprising;
        a convex surface of revolution about a centerline of said tip portion defined by an arc extending from a circumference of said needle body to the tip portion centerline;
        a relatively flat surface formed in the surface of revolution; and
    a port disposed in the flat surface, said port communicating with the needle body lumen; and
    a needle body curved portion disposed adjacent the tip portion and having a curvature in a plane not including said flat surface;
    said plane is perpendicular to said flat surface;
    said flat surface faces inwardly from an arc established by the needle body curved portion.

4. A multi-purpose phacoemulsification needle comprising:
    a needle body having a lumen therethrough for aspiration of fluid and tissue;
    a needle body proximate end adapted for attachment to a phacoemulsification handpiece;

a needle body distal end having a tip portion, said tip portion comprising;
　　a convex surface of revolution about a centerline of said tip portion defined by an arc extending from a circumference of said needle body to the tip portion centerline;
　　a relatively flat surface formed in the surface of revolution; and
　　a port disposed in the flat surface, said port communicating with the needle body lumen; and
a needle body curved portion disposed adjacent the tip portion and having a curvature in a plane not including said flat surface;
said plane is perpendicular to said flat surface;
said flat surface faces outwardly from an arc established by the needle body curved portion.

5. A multi-purpose phacoemulsification needle comprising:
　a needle body having a lumen therethrough for aspiration of fluid and tissue;
　a needle body proximal adapted for attachment to a phacoemulsification handpiece; and
　a needle body distal end having a tip portion, said tip portion comprising:
　　a rounded portion having sufficient surface area for polishing an eye lens capsule; and
　　a port disposed in said tip portion and communicating with the needle body lumen; and
　a needle body curved portion disposed adjacent the tip portion and having a curvature in a plane not including said flat surface;
　said plane is perpendicular to said flat surface;
　said flat surface faces inwardly from an arc established by the needle body curved portion.

6. A multi-purpose phacoemulsification needle comprising:
　a needle body having a lumen therethrough for aspiration of fluid and tissue;
　a needle body proximal adapted for attachment to a phacoemulsification handpiece; and
　a needle body distal end having a tip portion, said tip portion comprising:
　　a rounded portion having sufficient surface area for polishing an eye lens capsule; and
　　a port disposed in said tip portion and communicating with the needle body lumen; and
　a needle body curved portion disposed adjacent the tip portion and having a curvature in a plane not including said flat surface;
　said plane is perpendicular to said flat surface;
　said flat surface faces outwardly from an arc established by the needle body curved portion.

* * * * *